(12) United States Patent
Payne et al.

(10) Patent No.: US 9,499,791 B2
(45) Date of Patent: Nov. 22, 2016

(54) SKELETAL MUSCLE AUGMENTATION UTILIZING MUSCLE-DERIVED PROGENITOR COMPOSITIONS, AND TREATMENTS THEREOF

(75) Inventors: Thomas Payne, Pittsburgh, PA (US); Ronald Jankowski, Pittsburgh, PA (US); Ryan Pruchnic, Pittsburgh, PA (US); Michael Chancellor, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 993 days.

(21) Appl. No.: 12/245,379

(22) Filed: Oct. 3, 2008

(65) Prior Publication Data

US 2009/0098094 A1 Apr. 16, 2009
US 2016/0303169 A9 Oct. 20, 2016

Related U.S. Application Data

(63) Continuation-in-part of application No. 11/998,330, filed on Nov. 28, 2007, now Pat. No. 8,211,423.

(60) Provisional application No. 60/977,450, filed on Oct. 4, 2007, provisional application No. 60/867,405, filed on Nov. 28, 2006.

(51) Int. Cl.
 *A61K 35/34* (2006.01)
 *C12N 5/077* (2010.01)
 *A61K 35/12* (2015.01)

(52) U.S. Cl.
 CPC ............. *C12N 5/0659* (2013.01); *A61K 35/34* (2013.01); *C12N 5/0658* (2013.01); *A61K 35/12* (2013.01); *C12N 2500/84* (2013.01); *C12N 2501/70* (2013.01); *C12N 2510/00* (2013.01); *C12N 2533/54* (2013.01)

(58) Field of Classification Search
 CPC .. A61K 35/34; A61K 2300/00; A61K 35/12; C12N 5/0659; C12N 5/0692; C12N 2500/84; C12N 2533/54; C12N 5/0658; C12N 2501/70; G01N 33/6887
 See application file for complete search history.

(56) References Cited

U.S. PATENT DOCUMENTS

| | | |
|---|---|---|
| 4,424,208 A | 1/1984 | Wallace et al. |
| 4,965,353 A | 10/1990 | Della Valle et al. |
| 5,045,601 A | 9/1991 | Capelli et al. |
| 5,053,050 A | 10/1991 | Itay |
| 5,082,670 A | 1/1992 | Gage et al. |
| 5,130,141 A * | 7/1992 | Law et al. ............... 424/548 |
| 5,206,028 A | 4/1993 | Li |
| 5,336,263 A | 8/1994 | Ersek et al. |
| 5,443,950 A | 8/1995 | Naughton et al. |
| 5,510,254 A | 4/1996 | Naughton et al. |
| 5,516,532 A | 5/1996 | Atala et al. |
| 5,538,722 A | 7/1996 | Blau et al. |
| 5,541,107 A | 7/1996 | Naughton et al. |
| 5,594,032 A | 1/1997 | Gonzalez-Cadavid et al. |
| 5,656,478 A | 8/1997 | Tanagho et al. |
| 5,667,778 A | 9/1997 | Atala |
| 5,733,337 A | 3/1998 | Carr, Jr. et al. |
| 5,785,964 A | 7/1998 | Naughton et al. |
| 5,833,978 A | 11/1998 | Tremblay |
| 5,842,477 A | 12/1998 | Naughton et al. |
| 5,858,351 A | 1/1999 | Podskoff et al. |
| 5,858,390 A | 1/1999 | Boss |
| 5,858,721 A | 1/1999 | Naughton et al. |
| 5,863,531 A | 1/1999 | Naughton et al. |
| 5,869,041 A | 2/1999 | Vandenburgh |
| 5,876,447 A | 3/1999 | Arnett |
| 5,895,745 A * | 4/1999 | Chandler et al. ............... 435/2 |
| 5,902,741 A | 5/1999 | Purchio et al. |
| 5,962,325 A | 10/1999 | Naughton et al. |
| 6,001,654 A | 12/1999 | Anderson et al. |
| 6,099,832 A | 8/2000 | Mickle et al. |
| 6,121,042 A | 9/2000 | Peterson et al. |

(Continued)

FOREIGN PATENT DOCUMENTS

| | | |
|---|---|---|
| AU | 2001251599 B2 | 3/2006 |
| AU | 2006202380 A1 | 6/2006 |

(Continued)

OTHER PUBLICATIONS

Kuhl et al., 1986, Developmental Biology, 117: 628-635.*
Bonavaud et al. "Primary human muscle satellite cell culture: variations of cell yield, proliferation and differentiation rates according to age and sex of donors, site of muscle biopsy, and delay before processing." Biol Cell. Jun. 1997;89(3): pp. 233-240.*
Gibson et al. "Dermal Fibroblasts Converts to a Myogenic Lineage in mdx Mouse Muscle." *J. Cell Sol.* 108(1995):207-214.

(Continued)

*Primary Examiner* — Titilayo Moloye
(74) *Attorney, Agent, or Firm* — Goodwin Procter LLP; Shovon Ashraf (57) ABSTRACT

The present invention provides muscle-derived progenitor cells (MDCs) that show long-term survival following transplantation into body tissues and which can augment soft tissue following introduction into a site of soft tissue. Also provided are methods of isolating MDCs. The invention further provides methods of using compositions comprising MDCs for the augmentation and bulking of mammalian, including human, soft tissues in the treatment of various cosmetic or functional conditions, including malformation, injury, weakness, disease, or dysfunction. The invention also relates to uses of MDCs for the treatment of cosmetic or functional conditions, including, but not limited to skeletal muscle weakness, muscular dystrophy, muscle atrophy, spasticity, myoclonus and myalgia. The invention also relates to the use of MDCs for the increase of skeletal muscle.

12 Claims, 2 Drawing Sheets
(1 of 2 Drawing Sheet(s) Filed in Color)

(56) References Cited

U.S. PATENT DOCUMENTS

| | | |
|---|---|---|
| 6,171,340 B1 | 1/2001 | McDowell |
| 6,174,333 B1 | 1/2001 | Kadiyala et al. |
| 6,200,606 B1 | 3/2001 | Peterson et al. |
| 6,261,832 B1 | 7/2001 | Law |
| 6,299,905 B1 | 10/2001 | Peterson et al. |
| 6,306,424 B1 | 10/2001 | Vyakarnam et al. |
| 6,335,028 B1 | 1/2002 | Vogel et al. |
| 6,337,184 B1 | 1/2002 | Miller |
| 6,348,069 B1 | 2/2002 | Vacanti et al. |
| 6,482,645 B2 | 11/2002 | Atala |
| 6,497,872 B1 | 12/2002 | Weiss et al. |
| 6,503,504 B1 | 1/2003 | Vandenburgh |
| 6,682,761 B2 | 1/2004 | Pace et al. |
| 6,866,842 B1 | 3/2005 | Chancellor et al. |
| 6,986,735 B2 | 1/2006 | Abraham et al. |
| 7,141,072 B2 | 11/2006 | Geistlich et al. |
| 7,147,846 B2 | 12/2006 | Anderson et al. |
| 7,427,284 B2 | 9/2008 | Seedhom et al. |
| 7,887,792 B2 | 2/2011 | Chancellor et al. |
| 7,906,110 B2 | 3/2011 | Chancellor et al. |
| 8,105,834 B2 | 1/2012 | Chancellor et al. |
| 2002/0090389 A1 | 7/2002 | Humes et al. |
| 2002/0155096 A1 | 10/2002 | Chancellor et al. |
| 2003/0003085 A1 | 1/2003 | Kunkel et al. |
| 2004/0043008 A1 | 3/2004 | Vilquin et al. |
| 2005/0048039 A1 | 3/2005 | Dreyfus et al. |
| 2005/0220775 A1 | 10/2005 | Chancellor et al. |
| 2005/0238625 A1 | 10/2005 | Chancellor et al. |
| 2005/0265978 A1 | 12/2005 | Chancellor et al. |
| 2006/0078993 A1 | 4/2006 | Phan et al. |
| 2006/0280726 A1 | 12/2006 | Chancellor et al. |
| 2007/0065416 A1 | 3/2007 | Chancellor et al. |
| 2007/0065417 A1 | 3/2007 | Chancellor et al. |
| 2008/0152627 A1 | 6/2008 | Chancellor et al. |
| 2009/0010897 A1 | 1/2009 | Chancellor et al. |
| 2009/0155221 A1 | 6/2009 | Payne et al. |
| 2009/0221644 A1 | 9/2009 | Bradley et al. |
| 2011/0223139 A1 | 9/2011 | Chancellor et al. |
| 2012/0109107 A1 | 5/2012 | Chancellor et al. |

FOREIGN PATENT DOCUMENTS

| | | |
|---|---|---|
| CA | 2330660 A1 | 11/1999 |
| CA | 2406393 A1 | 10/2001 |
| CA | 2438904 A1 | 9/2002 |
| CN | 1812800 A | 8/2006 |
| EP | 1604674 A2 | 12/2005 |
| JP | 2000287683 A | 10/2000 |
| JP | 2004524029 A | 8/2004 |
| JP | 2007275613 A | 10/2007 |
| WO | 91/07992 | 6/1991 |
| WO | 94/07999 | 4/1994 |
| WO | 94/21299 | 9/1994 |
| WO | WO-9425080 A1 | 11/1994 |
| WO | 96/18303 | 6/1996 |
| WO | WO 96/39035 * | 12/1996 |
| WO | WO9639035 A1 * | 12/1996 |
| WO | 98/36055 | 8/1998 |
| WO | 98/44142 | 10/1998 |
| WO | 98/54301 | 12/1998 |
| WO | 99/47163 | 9/1999 |
| WO | WO-9946366 A1 | 9/1999 |
| WO | 99/56785 | 11/1999 |
| WO | 99/56786 A2 | 11/1999 |
| WO | 00/17322 A | 3/2000 |
| WO | 00/29552 A | 5/2000 |
| WO | 01/19966 | 3/2001 |
| WO | 01/78754 A2 | 10/2001 |
| WO | 02/067887 A2 | 9/2002 |
| WO | WO-02083864 A2 | 10/2002 |
| WO | WO-2004012503 A2 | 2/2004 |
| WO | WO-2004096245 A2 | 11/2004 |
| WO | WO-2008076435 A1 | 6/2008 |
| WO | WO-2008086040 A1 | 7/2008 |
| WO | 2008147314 A1 | 12/2008 |
| WO | WO-2008153813 A2 | 12/2008 |
| WO | WO-2010022083 A2 | 2/2010 |

OTHER PUBLICATIONS

Irintchey et al. "Ectopic Skeletal Muscles Derived from Myoblasts Implanted Under the Skin." J. Cell Sci. 111(1998):3287-3297.
Shafik. "Pelvic Double-Sphincter Control Complex." Urol. 23.6(1984):611-618.
Ding et al. "Bone Marrow Stromal Cells as a Vehicle for Gene Transfer." Gene Ther. 6(1999):1611-1616.
Katagiri et al., (1994). J. Cell Biol., 127:1755-1766.
Koretzky (1993). FASEB J., 7:420-426.
Kuby (1994). Immunology, 2nd Ed., WH Freeman Company, pp. 559-578.
Ledley (1996). Pharmaceutical Research, 13(11):1595-1614.
Lee et al., (2000). J. Cell Biol., 150(5):1085-1099.
Lee et al., (2001). J. Urology (Suppl.), 165:251 (Abstract 1033).
Lipton et al., (1979). Science, 205:1292-1294.
Lynch et al., (1992). Proc. Natl. Acad. Sci. USA, 89:1138-1142.
Madeiro et al., (2002). Clin. Exp. Obst. & Gyn., XXIX(2):117-120.
Martini et al., (1995). Anatomy and Physiology, 3rd Ed., Simon & Schuster Company, pp. 315-318.
Miller et al., (1999). Curr. Top. Dev. Biol., 43:191-219; see Table 3.
Kaufman et al. (1988), PNAS, 85:9606-9610.
Office Action issued for U.S. Appl. No. 11/505,735, Mail Date: Sep. 9, 2009.
Torrente et al. "Intraarterial Injection of Muscle-Derived CD34+Sca-1+ Stem Cells Restores Dystrophin in mdx Mice." J. Cell. Biol. 152.2(2001):335-348.
Chancellor et al., (2000), Neurourology and Urodynamics, 19(3):279-287.
Supplementary European Search Report, Appl. No. EP 02706457, Mailed on May 27, 2009.
Fukuda et al., (2000), Tanpakushita Kakusan Kouso (Protein, Nucleic Acid and Enzyme) 45(13), 2078-2084.
Ikada (2001), "Tissue Engineering—Toward Establishing of Basic Technology and Clinical Applications," Kagaku-Dojin Publishing Co., Inc. pp. 183-191.
Japanese Office Action, Application No. JP2002-567239, Date: Feb. 7, 2007 (with English Translation).
Pre-Appeal Examination Report, Appl. No. JP2002-567239, Date: Oct. 22, 2007 (with English Translation).
Andersson et al. "Advances in the Pharmacological Control of the Bladder." Exp. Physiol. 84 (1999) :195-213.
Acsadi et al., (1994). Hum. Mol. Genetics, 3(4):579-584.
Alden et al., (1999). Hum. Gene Ther., 10:2245-2253.
Anderson (1998). Nature, 392:25-30.
Andrews et al., (1986). Blood, 67:842-845.
Anwer et al., (1998). Hum. Gene Ther., 9:659-670.
Arcila et al., (1997). J. Neurobiol., 33:185-198.
Ashman et al., (1999). Int. J. Biochem. Cell. Biol. 31:1037-1051.
Atkins et al., (1999). Ann. Thorac. Surg., 67:124-129.
Atkins et al., (1999). J. Heart Lung Transplant., 18:1173-1180.
Bandara et al., (1993). Proc. Natl. Acad. Sci. USA, 90:10764-10768.
Baroffio et al., (1996). Differentiation, 60:47-57.
Barr & Leiden (1991). Science, 254:1507-1509.
Beauchamp et al., (1999). J. Cell Biol., 144:1113-1122.
Blanton et al. (1999). Muscle Nerve, 22:43-50.
Cannon et al., (2003). Urology, 62(5):958-963.
Chancellor et al., (2001). Trends Mol. Med., 7(7):301-306.
Civin et al., (1984). J. Immunol. 133:157-165.
Dalle et al., (1999). Gene Ther., 6:157-161.
Dana et al., (1998). Investigative Ophthalmology & Visual Science, 39:70-77.
Day et al., (1997). J. of Orthopedic Research, 15:894-903.
Deasy et al., (2002). Current Opinion in Molecular Therapeutics, 4:382-389.
Dhawan et al., (1992). Science, 254:1509-1512.
Dominov et al., (1998). J. Cell Biol., 142:537-544.
Faustman et al., (1991). Science, 252:1701.

(56) References Cited

OTHER PUBLICATIONS

Ferrari et al., (1998). Science, 279:1528-1530.
Fina et al., (1990). Blood, 75:2417-2426.
Friedmann (2000). Science, 287(5461):2163-2165.
Garban et al., (1997). Biol. Reprod., 56(4):954-963.
Grinnell A. D., (1994). Myology Ed. 2, A. G. Engel & C. F. Armstrong, McGraw-Hill, Inc., 303-304.
Gros et al., (1999). Hum. Gene Ther., 10:1207-1217.
Gross et al., (1999). Muscle & Nerve, 22:174-185.
Gussoni et al., (1992). Nature, 356:435-438.
Gussoni et al., (1999). Nature, 401:390-394.
Hortelano et al., (1999). Hum. Gene Ther., 10:1281-1288.
Huard et al., (1992). Muscle & Nerve, 15:550-560.
Huard et al., (1994). J. Clin. Invest., 93:586-599.
Huard et al., (1994). Muscle & Nerve, 17:224-234.
Huard et al., (1995). Gene Therapy, 2:107-115.
Huard et al., (1998). J. Urology, 159(5)Supplement:16 (Abstract 62).
Huard et al., (1998). J. Urology, 159:90 (Abstract 342).
Huard et al., (2002). Gene Ther., 9:1617-1626.
Irintchev et al., (1994). Dev. Dynam., 199:326-337.
Jackson et al., (1999). PNAS, 96(25):14482-14486.
Jankowski et al., (2001). Human Gene Therapy, 12:619-628.
Jiao et al., (1992). Brain Research, 575:143-147.
Jung et al., (1999). J. Urology, 162(1):204-212.
Karpati et al., (1993). Ann. Neurol., 34:8-17.
Kasemkijwattana et al., (1998). Cell Transplantation, 7(6):585-598.
Moisset et al., (1998). Biochem. Biophys. Res. Commun., 247:94-99.
Moisset et al., (1998). Gene Ther., 5:1340-1346.
Morgan et al., (1988). J. Neural. Sci., 86:137-147.
Murry et al., (1996). J. Clin. Invest., 98:2512-2523.
Musgrave et al., (1999). Gene Therapy & Molecular Biology, 3:207-220.
Newman et al., (2003). Am. J. Nurs., 103(8):46-55.
Nurcombe et al., (1985). Developmental Brain Research, 21:49-60 (Abstract).
Osawa et al., (1996). J. Immunol., 156:3207-3214.
Partridge et al., (1978). Nature, 73:306-308.
Partridge et al., (1989). Nature, 337:176-179.
Partridge T. A. & K. E. Davies, (1995). Brit. Med. Bulletin, 51:123-137.
Pittenger et al., (1999). Science, 284:143-147.
Price et al., (1987). Proc. Natl. Acad. Sci. USA, 84:156-160.
Qu et al., (1998). J. Cell Biol., 142(5):1257-1267.
Qu et al., (1999). Molec. Biol. of the Cell, 10:246a.
Rando et al., (1994). J. Cell Biol., 125(6):1275-1287.
Regulier et al., (1998). Gene Ther., 5:1014-1022.
Richler et al., (1970). Developmental Biology, 23:1-22.
Roman et al., (1992). Somat. Cell. Mol. Genet., 18:247-258.
Rosenberg et al., (2000). Science, 287:1751.
Sanes et al., (1986). EMBO J., 5:3133-3142.
Saini et al., (2006). Curr. Stem Cell Res. Ther., 1(2):157-171.
Seale et al., (2000). Developmental Biology, 218:115-124.
Simmons et al., (1991). Blood, 78:2848-2853.
Smith et al., (1997). Cell Growth and Differentiation, 8(8):927-934.
Spindler et al., (1995). J. of Orthopedic Research, 13:201-207.
Tirney et al., (2001). Mol. Urol. Spring, 5(1):37-43.
Tremblay et al., (1993). Cell Transplantation, 2:99-112.
Tremblay et al., (1997). Basic Appl. Myol., 7(3&4):221-230.
Tzeng et al., (1996). Surgery, 120(2):315-321.
Van De Rijn et al., (1989). Proc. Natl. Acad. Sci. USA, 86:4634-4638.
Vandenburgh (1996). Hum. Gene Ther., 7:2195-2200.
Verma (2000). Mol. Ther., 1:493.
Wang et al., (1997). Blood, 90:1075-1082.
Watt et al., (1984). Clin. Exp. Immunol., 55:419-426.
Webster et al., (1988). Exp. Cell. Res., 174:252-265.
Yamanishi et al., (2002). J. Urology, 168:2706-2710.
Yao et al., (1994). Gene Ther., 1:99-107.
Yokoyama et al., (1999). J. Urology, 161(4)Supplement:305 (Abstract 1775).
Yokoyama et al., (2000). World J. Urology, 18:56-61.
Yokoyama et al., (2001). J. Urology, 165:271-276.
Yokoyama et al., (2001). Urology, 57(4):826-831.
Yokoyama et al., (2001). Tissue Engineering, 7(4):395-404.
Yoshida et al., (1998). J. Cell Science. 111:769-779.
Young et al., (1993). In vitro Cell Dev. Biol., 29A:723-736.
Young et al., (1995). Dev. Dynam., 202:137-144.
Ziegler et al., (1999). Science, 285:1533-1558.
International Search Report for International Application No. PCT/US2008/011458, Mailed Feb. 17, 2009.
Rando et al. "Methods for Myoblast Transplantation." *Meth. Cell Biol.* 52(1998):261-272.
"Cell Potency." Wikipedia: The Free Encyclopedia. Wikimedia Foundation, Inc., Web. 2010. http://en.wikipedia.org/wiki/Cell_potency.
"Desmin." *Wikipedia: The Free Encyclopedia*. Wikimedia Foundation, Inc., Web. Nov. 17, 2012. http://en.wikipedia.org/wiki/Desmin.
"Stem Cells." www.nih.nih.gov/news/stemcell. (2001):ES1-10, 23-42, Appendix D.
"Urethra." MedicineNet. Mar. 19, 2012. Web. May 23, 2010. http://www.medterms.com/script/main/art.asp?articlekey=5907&pf=3&page=1.
Abraham et al. "Evaluation of the Porcine Intestinal Collagen Layer as a Biomaterial." *J. Biomed. Mat. Res.* 51.3(2000):442-452.
Abrams et al. "The Standardisation of Terminology of Lower Urinary Tract Function: Report From the Standardisation Sub-Committee of the International Continence Society." *Neurol. Urodynam.* 21.2(2002):167-178.
Adachi et al. "Muscle Derived, Cell Based Ex Vivo Gene Therapy for Treatment of Full Thickness Articular Cartilage Defects." *J. Rheumatol.* 29.9(2002):1920-1930.
Auger et al. "Tissue-Engineered Human Skin Substitutes Developed from Collagen-Populated Hydrated Gels: Clinical and Fundamental Applications." *Med. Biol. Eng. Comput.* 36(1998):801-812.
Baltoyannis et al. "Submucosa of Canine Small Intestine as an Alternative Medium-Diameter Autogenous Arterial Graft." *Int. Angiol.* 19.3(2000):280-284.
Bartynski et al. "Histopathologic Evaluation of Adipose Autografts in a Rabbit Ear Model." *Otolaryngol. Head Neck Surg.* 102(1990):314-321.
Battiston et al. "Nerve Repair by Means of Vein Filled with Muscle Grafts I. Clinical Results." *Microsurgery.* 20.1(2000):32-36.
Bayer. "Neuron Production in the Hippocampus and Olfactory Bulb of the Adult Rat Brain: Addition or Replacement?" *Ann. N. Y. Acad. Sci.* 457(1985):163-172.
Beets-Tan et al. "Measurement of Anal Sphincter Muscles: Endoanal US, Endoanal MR Imaging, or Phased-Array MR Imaging? A Study With Healthy Volunteers." *Radiology.* 220(2001):81-89.
Berjukow et al. "Membrane Properties of Single Muscle Cells of the Rhabdosphincter of the Male Urethra." *Prostate.* 58.3(2004):238-247.
Berman et al. "Comparative Cost Analysis of Collagen Injection and Fascia Lata Sling Cystourethropexy for the Treatment of Type III Incontinence in Women." *J. Urol.* 157(1997):122-124.
Berthod et al. "Collagen Synthesis by Fibroblasts Cultured with a Collagen Sponge." *Biomat.* 14.10(1993):749-754.
Berthod et al. "In vitro reconstructed Skin Models for Wound Coverage in Deep Burns." *Brit. J. Dermatol.* 136(1997):809-816.
Blight. "Miracles and Molecules—Progess in Spinal Cord Repair." *Nat. Neurosci.* 5(2002):1051-1054.
Boyce. "Cultured Skin Substitutes: A Review." *Tissue Eng.* 2.4(1996):255-266.
Carlson et al. "Prevention and Mangement of Incontinence Following Radical Prostatectomy." *Urol. Clin. North Am.* 28.3(2001):595-612.
Chajchir et al. "Fat Grafting Injection for Soft-Tissue Augmentation." *Plast. Reconstr. Surg.* 84(1989):921-935.
Chen et al. "High-Efficiency Transformation of Mammalian Cells by Plasmid DNA." *Mol. Cell. Biol.* 7.8(1987):2745-2752.

(56) References Cited

OTHER PUBLICATIONS

Cossu et al. "New Therapies for Muscular Dystrophy: Cautious Optimism." *Trends Mol. Med.* 10.10(2004):516-520.
Crisan et al. "Identification, Purification and Characterization of a Novel Population of CD146+CD133+ Myogenic Cells in Human Skeletal Muscle." *Orthopaedic Res. Soc. 53rd Annual Meeting* (Feb. 12-14, 2007). Paper #0040.
Deasy et al. "A Role for Cell Sex in Stem Cell Mediated Skeletal Muscle Regeneration: Female Cells Have Higher Muscle Regeneration Efficiency." *J. Cell. Biol.* 177.1(2007):73-86.
Deasy et al. "Mechanisms of Muscle Stem Cell Expansion with Cytokines." *Stem Cells.* 20(2002):50-60.
Dixon et al. "Recombinant Human Bone Morphogenetic Proteins-2 and -4 Induce Several Mesenchymal Phenotypes in Culture." *Wound Rep. Reg.* 4(1996):374-380.
Donovan et al. "The End of the Beginnings for Pluripotent Stem Cells." *Nature.* 414(2001):92-97.
Elia et al. "Genuine Stress Urinary Incontinence with Low Urethral Pressure: Five-Year Follow-Up After the Ball-Burch Procedure." *J. Repro. Med. Obst. Gynecologist.* 40.7(1995):503-506.
Ersek. "Transplantation of Purified Autologous Fat: A 3-Year Follow-Up Is Disappointing." *Plast. Reconstr. Surg.* 87(1991):219-228.
Fascetti-Leon et al. "Murine Muscle Precursor Cells Survived and Integrated in a Cryoinjured Gastroesophageal Junction." *J. Surg. Res.* 143.2(2007):253-259.
Fechheimer et al. "Transfection of Mammalian Cells with Plasmid DNA by Scrape Loading and Sonication Loading." *PNAS.* 84(1987):8463-8467.
Fraley et al. "Entrapment of a Bacterial Plasmid in Phospholipid Vesicles: Potential for Gene Transfer." *PNAS.* 76.7(1979):3348-3352.
Game et al. "Rejection Mechanisms in Transplantation." *Wien Klin Wochenschr.* 113(2001):823-838.
Gao et al. "The Dynamic in vivo Distribution of Bone Marrow-Derived Mesenchymal Stem Cells after Infusion." *Cells Tissues Organs.* 169(2001):12-20.
Germain et al. "Tissue Engineering of the Vascular System: From Capillaries to Larger Blood Vessels." *Med. Biol. Eng. Comput.* 38(2000):232-240.
Goldring et al. "Clinical Aspects, Pathology and Pathophysiology of Osteoarthritis." *J. Musculoskelet. Neuronal Interact.* 6.4(2006):376-378.
Goldring. "Are Bone Morphogenetic Proteins Effective Inducers of Cartilage Repair? Ex Vivo Transduction of Muscle-Derived Stem Cells." *Arthritis Rheum.* 54.2(2006):387-389.
Graham et al. "A New Technique for the Assay of Infectivity of Human Adenovirus 5 DNA." *Virol.* 52(1973):456-467.
Hansbrough et al. "Evaluation of a Biodegradable Matrix Containing Cultured Human Fibroblasts as a Dermal Replacement Beneath Meshed Skin Grafts on Athymic Mice." *Surg.* 111.1(1992):438-446.
Harland et al. "Translation of mRNA Injected into Xenopus Oocytes is Specifically Inhibited by Antisense RNA." *J. Cell. Biol.* 101.3(1985):1094-1099.
Höke. "Mechanisms of Disease: What Factors Limit the Success of Peripheral Nerve Regeneration in Humans?" *Nat. Clin. Pract. Neurol.* 2.8(2006):448-454.
Hörl et al. "Technique for Liposuction Fat Reimplantation and Long-Term Volume Evaluation by Magnetic Resonance Imaging." *Ann. Plast. Surg.* 26(1991):248-258.
Huard et al. "Differentiation of Primary Myoblast Injection Into the Lower Urinary Tract; Creation of Detrusor Cellular Myoplasty." *J. Urol.* 161.4S(1999):66. (Abstract #248).
Kaplan. "Neurogenesis in the 3-Month-Old Rat Visual Cortex." *J. Comp. Neurol.* 195.2(1981):323-338.
Kropp et al. "Bioengineering Organs Using Small Intestinal Submucosa Scaffolds: in Vivo Tissue Engineering Technology." *J. Endourol.* 14.1(2000):59-62.
Kropp et al. "Regenerative Urinary Bladder Augmentation Using Small Intestinal Submucosa: Urodynamic and Histopathologic Assessment in Long-Term Canine Bladder Augmentations." *J. Urol.* 155(1996):2098-2104.
Langer et al. "Tissue Engineering." *Science.* 260(1993):920-926.
Lee et al. "The Effects of Periurethral Muscle-Derived Stem Cell Injection on Leak Point Pressure in a Rat Model of Stress Urinary Incontinence." *Int. Urogynecol. J.* 14(2003):31-37.
Lucas et al. "A Population of Cells Resident Within Embryonic and Newborn Rat Skeletal Muscle is Capable of Differentiating into Multiple Mesodermal Phenotypes." *Wound Rep. Regen.* 3.4(1995):449-460.
Lucas et al. "Effect of Rat Mesenchymal Stem Cells on Development of Abdominal Adhesions After Surgery." *J. Surg. Res.* 62.2(1996):229-232.
Mak et al. "Injectable Filler Materials for Soft-Tissue Augmentation." *Otolaryngol. Clin. North Am.* 27.1(1994):211-222.
Mastrogiacomo et al. "Bone and Cartilage Formation by Skeletal Muscle Derived Cells." *J. Cell. Physiol.* 204.2(2005):594-603.
Menasché. "Skeletal Myoblasts as a Therapeutic Agent." *Prog. Cardiovasc. Dis.* 50.1(2007):7-17.
Minuth et al. "Tissue Engineering: Generation of Differentiated Artificial Tissues for Biomedical Applications." *Cell Tissue Res.* 291(1998):1-11.
Mouly et al. "Myoblast Transfer Therapy: Is There Any Light at the End of the Tunnel?" *Acta Myol.* 24.2(2005):128-133.
Mulcahy. "Erectile Function after Radical Prostatectomy." *Semin. Urol. Oncol.* 18.1(2000):71-75.
Naughton et al. "Human-Based Tissue Engineered Implants for Plastic and Reconstructive Surgery." *Clin. Plastic Surg.* 26.4(1999):579-586.
Nguyen et al. "Comparative Study of Survival of Autologous Adipose Tissue Taken and Transplanted by Different Techniques." *Plast. Recontr. Surg.* 85.3(1990):378-389.
Norris et al. "Peripheral Nerve Repair in Humans Using Muscle Autografts: A New Technique." *J. Bone Joint Surg. Br.* 70.4(1988):530-533.
Odorico et al. "Multilineage Differentiation from Human Embryonic Stem Cell Lines." *Stem Cells.* 19(2001):193-204.
Oshima et al. "Differential Myocardial Infarct Repair with Muscle Stem Cells Compared to Myoblasts." *Mol. Ther.* 12.6(2005):1130-1141.
Oshima et al. "Muscle Stem Cells Provide Superior Infarct Repair When Compared With Myoblasts." *Mol. Ther.* 11.S1(2005):S356. (Abstract #920).
Oshima et al. "Skeletal Muscle Stem Cells Acquire a Cardiac Phenotype and Display a Superior Ability for Cardiac Repair When Compared to Satellite Cell." *Japanese J. Thor. Cardiovasc. Surg.* 52(2004):192. (Abstract #PD4-2).
Payne et al. "A Relationship Between Vascular Endothelial Growth Factor, Angiogenesis, and Cardiac Repair After Muscle Stem Cell Transplantation Into Ischemic Hearts." *J. Am. College Cardiol.* 50.17(2007):1677-1684.
Payne et al. "Muscle Stem Cells Deliver Dystrophin and Adopt a Cardiac Phenotype Through Both Differentiation and Fusion in the Dystrophic (*mdx*) Heart." *Mol. Ther.* 9.S1(2004):S356. (Abstract #930).
Payne et al. "Muscle Stem Cells Genetically Modified to Express a VEGF Antagonist Display an Impaired Ability for Cardiac Repair." *Mol. Ther.* 11.S1(2005):S357. (Abstract #923).
Payne et al. "Muscle-Derived Stem Cells Express a Cardiac Phenotype Upon Transplantation into the Dystrophic Murine Heart." *Amer. Heart Assoc. Conf. Mol. Mechan. Growth Death Regen Myocard.* (2003)9. (Abstract #P42).
Payne et al. "Regeneration of Dystrophin-Expressing Myocytes in the mdx Heart by Skeletal Muscle Stem Cells." *Gene Ther.* 12.16(2005):1264-1274.
Payne et al. "VEGF Secretion by Skeletal Muscle-Derived Stem Cells Induces Angiogenesis, Prevents Remodeling, and Improves Function in Ischemic Hearts." *Circ. Res.* 99.5(2006):E22. (Abstract'#P17).
Peng et al. "Converse Relationship Between in Vitro Osteogenic Differentiation and in Vivo Bone Healing Elicited by Different (56) References Cited

OTHER PUBLICATIONS

Populations of Muscle-Derived Cells Genetically Engineered to Express BMP4." *J. Bone Min. Res.* 19.4(2004):630-641.
Pfister et al. "Assessment of the Intrinsic Urethral Sphincter Component Function in Postprostatectomy Urinary Incontinence." *Neurourol. Urodyn.* 21.3(2002):194-197.
Platt et al. "Knocking Out Xenograft Rejection." *Nat. Biotech.* 20.3(2002):231-232.
Potter et al. "Enhancer-Dependent Expression of Human κ Immunoglobulin Genes Introduced into Mouse Pre-B Lymphocytes by Electroporation." *PNAS.* 81(1984):7161-7165.
Qu-Petersen et al. "Identification of a Novel Population of Muscle Stem Cells in Mice: Potential for Muscle Regeneration." *J. Cell Biol.* 157(2002):851-864.
Qu-Petersen et al. "Muscle Derived Stem Cells Contribute to Blood Vessel and Peripheral Nerve Formation." *Mol. Biol. Cell.* 12(2001):366A-367A. (Abstract #2013).
Qu-Petersen et al. "Muscle Stem Cells Promote Nerve Regeneration and Contribute to the Development of Neuronal Tissues." *Exp. Hematol.* 31.7(2003):133. (Abstract # 218).
Rippe et al. "DNA-Mediated Gene Transfer into Adult Rat Hepatocytes in Primary Culture." *Mol. Cell. Biol.* 10.2(1990):689-695.
Sakai et al. "The Use of Ex Vivo Gene Transfer Based on Muscle-Derived Stem Cells for Cardiovascular Medicine." *Trends Cardiovasc. Med.* 12.3(2002):115-120.
Schmidt et al. "Neural Tissue Engineering: Strategies for Repair and Regeneration." *Annu. Rev. Biomed. Eng.* 5(2003):293-347.
Schäfer et al. "Anatomy of the Anal Sphincters." *Dis. Colon Rectum.* 37.8(1994):777-781. (Abstract Only).
Shapiro et al. "Novel Alginate Sponges for Cell Culture and Transplantation." *Biomat.* 18.8(1997):583-590.
Shen et al. "Structural and Functional Healing of Critical-Size Segmental Bone Defects by Transduced Muscle-Derived Cells Expressing BMP4." *J. Gene Med.* 6(2004):984-991.
Somogyi et al. "A Precise, Localized Bladder Injury Model to Investigate the Effect of Myoblast Injection on Bladder Contractility." *J. Urol.* 161.S4(1999):43. (Abstract #158).
Sun et al. "The Role of Muscle-Derived Stem Cells in Bone Tissue Engineering." *Biomaterials.* 26.18(2005):3953-3960.
't Hart et al. "The Use of Animal Models to Investigate the Pathogenesis of Neuroinflammatory Disorders of the Central Nervous System." *Curr. Opin. Neurol.* 16.3(2003):375-383.
Tirney et al. "Myoblast Periurethral Injection for the Treatment of Stress Urinary Incontinence." *J. Urol.* 159.S5(1998):327. (Abstract #1256).
Tokunaka et al. "Coexistence of Fast and Slow Myosin Isozymes in Human External Urethral Sphincter. A Preliminary Report" *J. Urol.* 138.3(1987):659-662.
Tremblay et al. "Results of Triple Blind Clinical Study of Myoblast Transplantations Without Immunosuppressive Treatment in Young Boys with Duchenne Muscular Dystrophy." *Cell Transplant.* 2(1993):99-112.

Tur-Kaspa et al. "Use of Electroporation to Introduce Biologically Active Foreign Genes into Primary Rat Hepatocytes." *Mol. Cell. Biol.* 6.2(1986):716-718.
Urish et al. "Muscle Stem Cells' High Regenerative Capacity Correlates With a High Resistance to Stress." *Orthopaedic Res. Soc. 52nd Annual Meeting* (Mar. 19-22, 2006). Paper #0337.
Urish et al. "Oxidative Stress Plays a Major Role in the Differential Repair of Skeletal and Cardiac Muscle Between Muscle Stem Cells and Myoblasts." *Orthopaedic Res. Soc. 53rd Annual Meeting* (Feb. 12-14, 2007). Paper #1225.
Urish et al. "The Role of Resistance to Inflammation and Oxidative Stress in Muscle Stem Cells' Increased Regenerative Capacity." *Int. Soc. Stem Cell Res.* (Jun. 29-Jul. 1, 2006). Poster Board # Sat-379.
van Wachem et al. "Myoblast Seeding in a Collagen Matrix Evaluated in vitro." *J. Biomed. Mat. Res.* 30(1996):353-360.
Watt et al. "Out of Eden: Stem Cells and Their Niches." *Science.* 287(2000):1427-1430.
Williams et al. "Cells Isolated from Adult Human Skeletal Muscle Capable of Differentiating into Multiple Mesodermal Phenotypes." *Am. Surg.* 65.1(1999):22-26.
Wu et al. "Evidence for Targeted Gene Delivery to Hep G2 Hepatoma Cells in Vitro." *Biochem.* 27.3(1988):887-892.
Wu et al. "Receptor-Mediated in Vitro Gene Transformation by a Soluble DNA Carrier System." *J. Biol. Chem.* 262.10(1987):4429-4432.
Yaffe. "Retention of Differentiation Potentialities During Prolonged Cultivation of Myogenic Cells." *PNAS.* 61(1968):477-483.
Yang et al."In vivo and in vitro Gene Transfer to Mammalian Somatic Cells by Particle Bombardment." *PNAS.* 87(1990):9568-9572.
Ye et al. "Tissue Engineering in Cardiovascular Surgery: New Approach to Develop Completely Human Autologous Tissue." *Eur. J. Cardio-Thorac. Surg.* 17(2000):449-454.
Yokoyama et al. "Primary Myoblast Injection Into the Urethra and Bladder as a Potential Treatment of Stress Urinary Incontinence and Impaired Detrusor Contractility; Long Term Survival Without Significant Cytotoxicity." *J. Urol.* 161.S4(1999):307. (Abstract #1182).
Young et al. "Human Reserve Pluripotent Mesenchymal Stem Cells are Present in the Connective Tissues of Skeletal Muscle and Dermis Derived from Fetal, Adult, and Geriatric Donors." *Anat Rec.* 264.1(2001):51-62.
Young et al. "Muscle-Based Gene Therapy and Tissue Engineering to Improve Bone Healing." *Clin. Orthop. Relat. Res.* 403S(2002):S243-S251.
Young et al. "Use of Mesenchymal Stem Cells in a Collagen Matrix for Achilles Tendon Repair." *J. Orthop. Res.* 16.4(1998):406-413.
Zheng et al. "Multi-Potency of Myo-Endothelial Clones Isolated From Adult Human Skeletal Muscle." *Orthopaedic Res. Soc.* 53rd Annual Meeting (Feb. 12-14, 2007). Paper #0421.
Zhuqing Qu et al. "Identification of Muscle-Derived Stem Cells." *Mol. Biol. Cell.* 10(1999):246a.
Markert, Chad D. et al., "Mesenchymal Stem Cells: Emerging Therapy for Duchenne Muscular Dystrophy," PM&R, vol. 1(6):547-559 (2009).
Japanese Office Action for Application No. 2010-527998, 6 pages, dated Jun. 6, 2014.

* cited by examiner

SKELETAL MUSCLE AUGMENTATION UTILIZING MUSCLE-DERIVED PROGENITOR COMPOSITIONS, AND TREATMENTS THEREOF

RELATED APPLICATIONS

This application claims benefit of priority from U.S. Provisional Application No. 60/977,450, filed on Oct. 4, 2007, the disclosure of which is incorporated by reference in its entirety; this application is a continuation-in-part of U.S. patent application No. 11/998,330 (now U.S. Pat. No. 8,211, 423), filed Nov. 28, 2007, which claims priority from U.S. Provisional Application No. 60/867,405, filed on Nov. 28, 2006.

GOVERNMENT INTERESTS

This invention was made with Government support under Grant No. DK055387 awarded by the National Institutes of Health. The Government has certain rights to this invention.

FIELD OF THE INVENTION

The present invention relates to muscle-derived progenitor cells (MDCs) and compositions of MDCs and their use in the augmentation of body tissues, particularly skeletal muscle. In particular, the present invention relates to muscle-derived progenitor cells that show long-term survival following introduction into skeletal muscle, methods of isolating MDCs and methods of using MDC-containing compositions for the augmentation of human or animal skeletal muscle. The invention also relates to novel uses of muscle-derived progenitor cells for the treatment of cosmetic or functional conditions, including, but not limited to skeletal muscle weakness, muscular dystrophy, muscle atrophy, spasticity, myoclonus and myalgia. The invention also relates to the novel use of MDCs for the increase of skeletal muscle mass in athletes or other organisms in need of greater than average skeletal muscle mass.

BACKGROUND OF THE INVENTION

Myoblasts, the precursors of muscle fibers, are mononucleated muscle cells that fuse to form post-mitotic multinucleated myotubes, which can provide long-term expression and delivery of bioactive proteins (T. A. Partridge and K. E. Davies, 1995, Brit. Med. Bulletin 51:123 137; J. Dhawan et al., 1992, Science 254: 1509 12; A. D. Grinnell, 1994, Myology Ed 2, A. G. Engel and C. F. Armstrong, McGraw-Hill, Inc., 303 304; S. Jiao and J. A. Wolff, 1992, Brain Research 575:143 7; H. Vandenburgh, 1996, Human Gene Therapy 7:2195 2200).

Cultured myoblasts contain a subpopulation of cells that show some of the self-renewal properties of stem cells (A. Baroffio et al., 1996, Differentiation 60:47 57). Such cells fail to fuse to form myotubes, and do not divide unless cultured separately (A. Baroffio et al., supra). Studies of myoblast transplantation (see below) have shown that the majority of transplanted cells quickly die, while a minority survive and mediate new muscle formation (J. R. Beuchamp et al., 1999, J. Cell Biol. 144:1113 1122). This minority of cells shows distinctive behavior, including slow growth in tissue culture and rapid growth following transplantation, suggesting that these cells may represent myoblast stem cells (J. R. Beuchamp et al., supra).

Myoblasts have been used as vehicles for gene therapy in the treatment of various muscle- and non-muscle-related disorders. For example, transplantation of genetically modified or unmodified myoblasts has been used for the treatment of Duchenne muscular dystrophy (E. Gussoni et al., 1992, Nature, 356:435 8; J. Huard et al., 1992, Muscle & Nerve, 15:550 60; G. Karpati et al., 1993, Ann. Neurol., 34:8 17; J. P. Tremblay et al., 1993, Cell Transplantation, 2:99 112; P. A. Moisset et al., 1998, Biochem. Biophys. Res. Commun. 247:94 9; P. A. Moisset et al., 1998, Gene Ther. 5:1340 46). In addition, myoblasts have been genetically engineered to produce proinsulin for the treatment of Type 1 diabetes (L. Gros et al., 1999, Hum. Gen. Ther. 10:1207 17); Factor IX for the treatment of hemophilia B (M. Roman et al., 1992, Somat. Cell. Mol. Genet. 18:247 58; S. N. Yao et al., 1994, Gen. Ther. 1:99 107; J. M. Wang et al., 1997, Blood 90:1075 82; G. Hortelano et al., 1999, Hum. Gene Ther. 10:1281 8); adenosine deaminase for the treatment of adenosine deaminase deficiency syndrome (C. M. Lynch et al., 1992, Proc. Natl. Acad. Sci. USA, 89:1138 42); erythropoietin for the treatment of chronic anemia (E. Regulier et al., 1998, Gene Ther. 5:1014 22; B. Dalle et al., 1999, Gene Ther. 6:157 61), and human growth hormone for the treatment of growth retardation (K. Anwer et al., 1998, Hum. Gen. Ther. 9:659 70).

Myoblasts have also been used to treat muscle tissue damage or disease, as disclosed in U.S. Pat. No. 5,130,141 to Law et al., U.S. Pat. No. 5,538,722 to Blau et al., and U.S. Pat. No. 6,866,842 by Chancellor et al incorporated by reference herein. In addition, myoblast transplantation has been employed for the repair of myocardial dysfunction (C. E. Murry et al., 1996, J. Clin. Invest. 98:2512 23; B. Z. Atkins et al., 1999, Ann. Thorac. Surg. 67:124 129; B. Z. Atkins et al., 1999, J. Heart Lung Transplant. 18:1173 80).

In spite of the above, in most cases, primary myoblast-derived treatments have been associated with low survival rates of the cells following transplantation due to migration and/or phagocytosis. To circumvent this problem, U.S. Pat. No. 5,667,778 to Atala, incorporated by reference herein, discloses the use of myoblasts suspended in a liquid polymer, such as alginate. The polymer solution acts as a matrix to prevent the myoblasts from migrating and/or undergoing phagocytosis after injection. However, the polymer solution presents the same problems as the biopolymers discussed above. Furthermore, the Atala patent is limited to uses of myoblasts in only muscle tissue, but no other tissue.

Thus, there is a need for other, different tissue augmentation materials that are long-lasting, compatible with a wide range of host tissues, and which cause minimal inflammation, scarring, and/or stiffening of the tissues surrounding the implant site. Accordingly, the muscle-derived progenitor cell (MDC)-containing compositions of the present invention are provided as improved and novel materials for augmenting skeletal muscle. Further provided are methods of producing muscle-derived progenitor cell compositions that show long-term survival following transplantation, and methods of utilizing MDCs and compositions containing MDCs to treat various aesthetic and/or functional defects, including, but not limited to, skeletal muscle weakness, muscular dystrophy, muscle atrophy, spasticity, myoclonus and myalgia. Also provided are methods of using MDCs and compositions containing MDCs for the increase of skeletal muscle mass in athletes or other organisms in need of greater than average skeletal muscle mass.

It is notable that prior attempts to use myoblasts for non-muscle tissue augmentation were unsuccessful (U.S. Pat. No. 5,667,778 to Atala). Therefore, the findings disclosed herein are unexpected, as they show that the muscle-derived progenitor cells according to the present invention can be successfully transplanted into non-muscle tissue, including skeletal muscle tissue, and exhibit long-term survival. As a result, MDCs and compositions comprising MDCs can be used as a general augmentation material for skeletal muscle production. Moreover, since the muscle-derived progenitor cells and compositions of the present invention can be derived from autologous sources, they carry a reduced risk of immunological complications in the host, including the reabsorption of augmentation materials, and the inflammation and/or scarring of the tissues surrounding the implant site.

Although mesenchymal stem cells can be found in various connective tissues of the body including muscle, skeletal muscle, cartilage, etc. (H. E. Young et al., 1993, In vitro Cell Dev. Biol. 29A:723 736; H. E. Young, et al., 1995, Dev. Dynam. 202:137 144), the term mesenchymal has been used historically to refer to a class of stem cells purified from skeletal muscle marrow, and not from muscle. Thus, mesenchymal stem cells are distinguished from the muscle-derived progenitor cells of the present invention. Moreover, mesenchymal cells do not express the CD34 cell marker (M. F. Pittenger et al., 1999, Science 284:143 147), which is expressed by the muscle-derived progenitor cells described herein.

The description herein of disadvantages and problems associated with known compositions, and methods is in no way intended to limit the scope of the embodiments described in this document to their exclusion. Indeed, certain embodiments may include one or more known compositions, compounds, or methods without suffering from the so-noted disadvantages or problems.

SUMMARY OF THE INVENTION

It is an object of the present invention to provide novel muscle-derived progenitor cells (MDCs) and MDC compositions exhibiting long-term survival following transplantation. The MDCs of this invention and compositions containing the MDCs comprise early progenitor muscle cells, i.e., muscle-derived stem cells that express progenitor cell markers, including, but not limited to desmin, M-cadherin, MyoD, myogenin, CD34, and Bcl-2. In addition, these early progenitor muscle cells express the Flk-1, Sca-1, MNF, and c-met cell markers, but do not express the CD45 or c-Kit cell markers.

It is another object of the present invention to provide methods for isolating and enriching muscle-derived progenitor cells from a starting muscle cell population. These methods result in the enrichment of MDCs that have long-term survivability after transplantation or introduction into a site of soft tissue. The MDC population according to the present invention is particularly enriched with cells that express progenitor cell markers, including, but not limited to desmin, M-cadherin, MyoD, myogenin, CD34, and Bcl-2. This MDC population also expresses the Flk-1, Sca-1, MNF, and c-met cell markers, but does not express the CD45 or c-Kit cell markers.

It is yet another object of the present invention to provide methods of using MDCs and compositions comprising MDCs for the augmentation of muscle tissue, including skeletal muscle, without the need for polymer carriers or special culture media for transplantation. Such methods include the administration of MDC compositions by introduction into skeletal muscle, for example by direct injection into or on the surface of the tissue, or by systemic distribution of the compositions.

It is yet another object of the present invention to provide methods of augmenting skeletal muscle, following injury, wounding, surgeries, traumas, non-traumas, or other procedures that result in fissures, openings, depressions, wounds, and the like.

It is a further object of the present invention to provide MDCs and compositions comprising MDCs that are modified through the use of chemicals, growth media, and/or genetic manipulation. Such MDCs and compositions thereof comprise chemically or genetically modified cells useful for the production and delivery of biological compounds, and the treatment of various diseases, conditions, injuries, or illnesses.

It is a further object of the present invention to provide MDCs and compositions comprising MDCs that are modified through the use of chemicals, growth media, and/or genetic manipulation. Such MDCs and compositions thereof comprise chemically or genetically modified cells useful for the production and delivery of biological compounds, and the treatment of various diseases, conditions, injuries, or illnesses.

It is yet another embodiment of the invention to provide pharmaceutical compositions comprising MDCs and compositions comprising MDCs. These pharmaceutical compositions comprise isolated MDCs. These MDCs may be subsequently expanded by cell culture after isolation. In one aspect of this embodiment, these MDCs are frozen prior to delivery to a subject in need of the pharmaceutical composition.

The invention also provides compositions and methods involving the isolation of MDCs using a single plating technique. MDCs are isolated from a biopsy of skeletal muscle. In one embodiment, the skeletal muscle from the biopsy may be stored for 1-6 days. In one aspect of this embodiment, the skeletal muscle from the biopsy is stored at 4° C. The cells are minced, and digested using a collagenase, dispase, another enzyme or a combination of enzymes. After washing the enzyme from the cells, the cells are cultured in a flask in culture medium for between about 30 and about 120 minutes. During this period of time, the "rapidly adhering cells" stick to the walls of the flask or container, while the "slowly adhering cells" or MDCs remain in suspension. The "slowly adhering cells" are transferred to a second flask or container and cultured therein for a period of 1-3 days. During this second period of time the "slowly adhering cells" or MDCs stick to the walls of the second flask or container.

In another embodiment of the invention, these MDCs are expanded to any number of cells. In a preferred aspect of this embodiment, the cells are expanded in new culture media for between about 10 and 20 days. More preferably, the cells are expanded for 17 days.

The MDCs, whether expanded or not expanded, may be preserved in order to be transported or stored for a period of time before use. In one embodiment, the MDCs are frozen. Preferably, the MDCs are frozen at between about −20 and −90° C. More preferably, the MDCs are frozen at about −80° C. These frozen MDCs are used as a pharmaceutical composition.

MDCs, whether frozen or preserved as a pharmaceutical composition, or used fresh, may be used to treat a number of skeletal muscle degenerative pathologies. These conditions include but are not limited to skeletal muscle weakness, muscular dystrophy, muscle atrophy, spasticity, myoclonus and myalgia. MDCs, whether frozen or preserved as a pharmaceutical composition, or used fresh, may also be used for the increase of skeletal muscle mass in athletes or other organisms in need of greater than average skeletal muscle mass.

Additional objects and advantages afforded by the present invention will be apparent from the detailed description and exemplification herein below.

BRIEF DESCRIPTION OF THE DRAWINGS

The patent or patent application file contains at least one photographic reproduction executed in color. Copies of this patent or patent application with color photographic reproduction(s) will be provided by the U.S. Patent and Trademark Office upon request and payment of the necessary fee.

The appended figures are presented to further describe the invention and to assist in its understanding through clarification of its various aspects.

DETAILED DESCRIPTION OF THE INVENTION

The invention provides human MDCs and methods of using such cells to generate skeletal muscle tissue to repair damaged skeletal muscle or to increase skeletal muscle volume and/or strength to above wild type levels. The invention further provides methods of treating skeletal muscle disorders including but not limited to skeletal muscle weakness, muscular dystrophy, muscle atrophy, spasticity, myoclonus and myalgia. The isolation of human muscle-derived cells (MDCs) from adult tissue are capable of achieving increased skeletal muscle density and skeletal muscle volume within human subjects administered these cells.

Muscle-Derived Cells and Compositions

The present invention provides MDCs comprised of early progenitor cells (also termed muscle-derived progenitor cells or muscle-derived stem cells herein) that show long-term survival rates following transplantation into body tissues, preferably skeletal muscle. To obtain the MDCs of this invention, a muscle explant, preferably skeletal muscle, is obtained from an animal donor, preferably from a mammal, including humans. This explant serves as a structural and functional syncytium including "rests" of muscle precursor cells (T. A. Partridge et al., 1978, Nature 73:306 8; B. H. Lipton et al., 1979, Science 205:12924).

Cells isolated from primary muscle tissue contain mixture of fibroblasts, myoblasts, adipocytes, hematopoietic, and muscle-derived progenitor cells. The progenitor cells of a muscle-derived population can be enriched using differential adherence characteristics of primary muscle cells on collagen coated tissue flasks, such as described in U.S. Pat. No. 6,866,842 of Chancellor et al, incorporated herein by reference. Cells that are slow to adhere tend to be morphologically round, express high levels of desmin, and have the ability to fuse and differentiate into multinucleated myotubes U.S. Pat. No. 6,866,842 of Chancellor et al.). A subpopulation of these cells was shown to respond to recombinant human skeletal muscle morphogenic protein 2 (rhBMP-2) in vitro by expressing increased levels of alkaline phosphatase, parathyroid hormone dependent 3',5'-cAMP, and other markers of osteogenic and myogenic lineages (U.S. Pat. No. 6,866,842 of Chancellor et al.; T. Katagiri et al., 1994, J. Cell Biol., 127:1755 1766).

In one embodiment of the invention, a preplating procedure may be used to differentiate rapidly adhering cells from slowly adhering cells (MDCs). In accordance with the present invention, populations of rapidly adhering MDC (PP1-4) and slowly adhering, round MDC (PP6) were isolated and enriched from skeletal muscle explants and tested for the expression of various markers using immunohistochemistry to determine the presence of pluripotent cells among the slowly adhering cells (Example 1; U.S. Pat. No. 6,866,842 to Chancellor et al.). As shown in Table 1, Example 1 herein, the PP6 cells expressed myogenic markers, including desmin, MyoD, and Myogenin. The PP6 cells also expressed c-met and MNF, two genes that are expressed at an early stage of myogenesis (J. B. Miller et al., 1999, Curr. Top. Dev. Biol. 43:191 219; see Table 3). The PP6 showed a lower percentage of cells expressing M-cadherin, a satellite cell-specific marker (A. Irintchev et al., 1994, Development Dynamics 199:326 337), but a higher percentage of cells expressing Bcl-2, a marker limited to cells in the early stages of myogenesis (J. A. Dominov et al., 1998, J. Cell Biol. 142:537 544). The PP6 cells also expressed CD34, a marker identified with human hematopoietic progenitor cells, as well as stromal cell precursors in skeletal muscle marrow (R. G. Andrews et al., 1986, Blood 67:842 845; C. I. Civin et al., 1984, J. Immunol. 133:157 165; L. Fina et al, 1990, Blood 75:2417 2426; P. J. Simmons et al., 1991, Blood 78:2848 2853; see Table 3). The PP6 cells also expressed Flk-1, a mouse homologue of human KDR gene which was recently identified as a marker of hematopoietic cells with stem cell-like characteristics (B. L. Ziegler et al., 1999, Science 285:1553 1558; see Table 3). Similarly, the PP6 cells expressed Sca-1, a marker present in hematopoietic cells with stem cell-like characteristics (M. van de Rijn et al., 1989, Proc. Natl. Acad. Sci. USA 86:4634 8; M. Osawa et al., 1996, J. Immunol. 156:3207 14; see Table 3). However, the PP6 cells did not express the CD45 or c-Kit hematopoietic stem cell markers (reviewed in L K. Ashman, 1999, Int. J. Biochem. Cell. Biol. 31:1037 51; G. A. Koretzky, 1993, FASEB J. 7:420 426; see Table 3).

In one embodiment of the present invention, the PP6 population of muscle-derived progenitor cells having the characteristics described herein are provided. These muscle-derived progenitor cells express the desmin, CD34, and Bcl-2 cell markers. In accordance with the present invention, the PP6 cells are isolated by the techniques described herein (Example 1) to obtain a population of muscle-derived progenitor cells that have long-term survivability following transplantation. The PP6 muscle-derived progenitor cell population comprises a significant percentage of cells that express progenitor cell markers, including, but not limited to desmin, CD34, and Bcl-2. In addition, PP6 cells express the Flk-1 and Sca-1 cell markers, but do not express the CD45 or c-Kit markers. Preferably, greater than 95% of the PP6 cells express the desmin, Sca-1, and Flk-1 markers, but do not express the CD45 or c-Kit markers. It is preferred that the PP6 cells are utilized within about 1 day or about 24 hours after the last plating.

In a preferred embodiment, the rapidly adhering cells and slowly adhering cells (MDCs) are separated from each other using a single plating technique. One such technique is described in Example 2. First, cells are provided from a skeletal muscle biopsy. The biopsy need only contain about 100 mg of cells. Biopsies ranging in size from about 50 mg to about 500 mg are used according to both the pre-plating and single plating methods of the invention. Further biopsies of 50, 100, 110, 120, 130, 140, 150, 200, 250, 300, 400 and 500 mg are used according to both the pre-plating and single plating methods of the invention.

In a preferred embodiment of the invention, the tissue from the biopsy is then stored for 1 to 7 days. This storage is at a temperature from about room temperature to about 4° C. This waiting period causes the biopsied skeletal muscle tissue to undergo stress. While this stress is not necessary for the isolation of MDCs using this single plate technique, using the wait period generally results in a greater yield of MDCs.

According to preferred embodiments, tissue from the biopsies is minced and centrifuged. The pellet is resuspended and digested using a digestion enzyme. Enzymes that may be used include, but are not limited to, collagenase, dispase or combinations of these enzymes. After digestion, the enzyme is washed off of the cells. The cells are transferred to a flask in culture media for the isolation of the rapidly adhering cells. Many culture media may be used. Particularly preferred culture media include those that are designed for culture of endothelial cells including Cambrex Endothelial Growth Medium. This medium may be supplemented with other components including fetal bovine serum, IGF-1, bFGF, VEGF, EGF, hydrocortisone, heparin, and/or ascorbic acid. Other media that may be used in the single plating technique include InCell M310F medium. This medium may be supplemented as described above, or used unsupplemented.

The step for isolation of the rapidly adhering cells may require culture in flask for a period of time from about 30 to about 120 minutes. The rapidly adhering cells adhere to the flask in 30, 40, 50, 60, 70, 80, 90, 100, 110 or 120 minutes. After they adhere, the slowly adhering cells are separated from the rapidly adhering cells from removing the culture media from the flask to which the rapidly adhering cells are attached to.

The culture medium removed from this flask is then transferred to a second flask. The cells may be centrifuged and resuspended in culture medium before being transferred to the second flask. The cells are cultured in this second flask for between 1 and 3 days. Preferably, the cells are cultured for two days. During this period of time, the slowly adhering cells (MDCs) adhere to the flask. After the MDCs have adhered, the culture media is removed and new culture media is added in order to promote expansion of the MDCs. The MDCs may be expanded in number by culturing them for from about 10 to about 20 days. The MDCs may be expanded in number by culturing them for 10, 11, 12, 13, 14, 15, 16, 17, 18, 19 or 20 days. Preferably, the MDCs are subject to expansion culture for 17 days.

As an alternative to the pre-plating and single plating methods, the MDCs of the present invention can be isolated by fluorescence-activated cell sorting (FACS) analysis using labeled antibodies against one or more of the cell surface markers expressed by the MDCs (C. Webster et al., 1988, Exp. Cell. Res. 174:252 65; J. R. Blanton et al., 1999, Muscle Nerve 22:43 50). For example, FACS analysis can be performed using labeled antibodies that specifically bind to CD34, Flk-1, Sca-1, and/or the other cell-surface markers described herein to select a population of PP6-like cells that exhibit long-term survivability when introduced into the host tissue. Also encompassed by the present invention is the use of one or more fluorescence-detection labels, for example, fluorescein or rhodamine, for antibody detection of different cell marker proteins.

Using any of the MDCs isolation methods described above, or otherwise known in the art, MDCs that are to be transported, or are not going to be used for a period of time may be preserved using any method known in the art. For example, the isolated MDCs may be frozen to a temperature ranging from about −25 to about −90° C. Preferably, the MDCs are frozen at about −80° C. on dry ice for delayed use or transport. The freezing may be done with any cryopreservation medium known in the art.

Muscle-Derived Cell-Based Treatments

In one embodiment of the present invention, the MDCs are isolated from a skeletal muscle source and introduced or transplanted into a muscle or non-muscle soft tissue site of interest, or into skeletal muscle. Advantageously, the MDCs of the present invention are isolated and enriched to contain a large number of progenitor cells showing long-term survival following transplantation. In addition, the muscle-derived progenitor cells of this invention express a number of characteristic cell markers, such desmin, CD34, and Bcl-2. Furthermore, the muscle-derived progenitor cells of this invention express the Sca-1, and Flk-1 cell markers, but do not express the CD45 or c-Kit cell markers (see Example 1).

MDCs and compositions comprising MDCs of the present invention can be used to repair, treat, or ameliorate various aesthetic or functional conditions (e.g. defects) through the augmentation of skeletal muscle. In particular, such compositions can be used for the treatment of skeletal muscle disorders. Multiple and successive administrations of MDC are also embraced by the present invention.

For MDC-based treatments, a skeletal muscle explant is preferably obtained from an autologous or heterologous human or animal source. An autologous animal or human source is more preferred. MDC compositions are then prepared and isolated as described herein. To introduce or transplant the MDCs and/or compositions comprising the MDCs according to the present invention into a human or animal recipient, a suspension of mononucleated muscle cells is prepared. Such suspensions contain concentrations of the muscle-derived progenitor cells of the invention in a physiologically-acceptable carrier, excipient, or diluent. For example, suspensions of MDC for administering to a subject can comprise $10^8$ to $10^9$ cells/ml in a sterile solution of complete medium modified to contain the subject's serum, as an alternative to fetal bovine serum. Alternatively, MDC suspensions can be in serum-free, sterile solutions, such as cryopreservation solutions (Celox Laboratories, St. Paul, Minn.). The MDC suspensions can then be introduced e.g., via injection, into one or more sites of the donor tissue.

The described cells can be administered as a pharmaceutically or physiologically acceptable preparation or composition containing a physiologically acceptable carrier, excipient, or diluent, and administered to the tissues of the recipient organism of interest, including humans and non-human animals. The MDC-containing composition can be prepared by resuspending the cells in a suitable liquid or solution such as sterile physiological saline or other physiologically acceptable injectable aqueous liquids. The amounts of the components to be used in such compositions can be routinely determined by those having skill in the art.

The MDCs or compositions thereof can be administered by placement of the MDC suspensions onto absorbent or adherent material, e.g., a collagen sponge matrix, and insertion of the MDC-containing material into or onto the site of interest. Alternatively, the MDCs can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the MDCs can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

To optimize transplant success, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the transplant procedure. For example, cyclosporin A or other immunosuppressive drugs can be administered to the transplant recipient. Immunological tolerance may also be induced prior to transplantation by alternative methods known in the art (D. J. Watt et al., 1984, Clin. Exp. Immunol. 55:419; D. Faustman et al., 1991, Science 252:1701).

Consistent with the present invention, the MDCs can be administered to body tissues, including skeletal muscle. The number of cells in an MDC suspension and the mode of administration may vary depending on the site and condition being treated. From about $1.0 \times 10^5$ to about $1 \times 10^8$ MDCs may be administered according to the invention. As a non-limiting example, in accordance with the present invention, about $0.5$-$2.0 \times 10^6$ MDCs are administered via a collagen sponge matrix for the treatment of an approximately 5 mm region of skull defect (see Example 3).

For skeletal muscle augmentation or treatment of skeletal muscle disorders, the MDCs are prepared as described above and are administered, e.g. via injection, onto, into or around skeletal muscle tissue to provide additional skeletal muscle strength and/or volume. As is appreciated by the skilled practitioner, the number of MDC introduced is modulated to provide varying amounts of skeletal muscle density and/or skeletal muscle volume, as needed or required. Thus, the present invention also embraces the use of MDC of the invention in treating skeletal muscle disorders or enhancing skeletal muscle density and/or skeletal muscle volume. Skeletal muscle disorders include but are not limited to skeletal muscle weakness, muscular dystrophy, muscle atrophy, spasticity, myoclonus and myalgia. The invention also relates to the novel use of MDCs for the increase of skeletal muscle mass in athletes or other organisms in need of greater than average skeletal muscle mass.

Genetically Engineered Muscle-Derived Cells

In another aspect of the present invention, the MDCs of this invention may be genetically engineered to contain a nucleic acid sequence(s) encoding one or more active biomolecules, and to express these biomolecules, including proteins, polypeptides, peptides, hormones, metabolites, drugs, enzymes, and the like. Such MDCs may be histocompatible (autologous) or nonhistocompatible (allogeneic) to the recipient, including humans. These cells can serve as long-term local delivery systems for a variety of treatments, for example, for the treatment of skeletal muscle diseases and pathologies, including, but not limited to skeletal muscle weakness, muscular dystrophy, muscle atrophy, spasticity, myoclonus and myalgia.

Preferred in the present invention are autologous muscle-derived progenitor cells, which will not be recognized as foreign to the recipient. In this regard, the MDC used for cell-mediated gene transfer or delivery will desirably be matched vis-a-vis the major histocompatibility locus (MHC or HLA in humans). Such MHC or HLA matched cells may be autologous. Alternatively, the cells may be from a person having the same or a similar MHC or HLA antigen profile. The patient may also be tolerized to the allogeneic MHC antigens. The present invention also encompasses the use of cells lacking MHC Class I and/or II antigens, such as described in U.S. Pat. No. 5,538,722, incorporated herein by reference.

The MDCs may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. MDCs can be transfected or transduced by different vectors and thus can serve as gene delivery vehicles to transfer the expressed products into muscle.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, and the like.

Vectors for introducing heterologous (i.e., foreign) nucleic acid (DNA or RNA) into muscle cells for the expression of bioactive products are well known in the art. Such vectors possess a promoter sequence, preferably, a promoter that is cell-specific and placed upstream of the sequence to be expressed. The vectors may also contain, optionally, one or more expressible marker genes for expression as an indication of successful transfection and expression of the nucleic acid sequences contained in the vector.

Illustrative examples of vehicles or vector constructs for transfection or infection of the muscle-derived cells of the present invention include replication-defective viral vectors, DNA virus or RNA virus (retrovirus) vectors, including, but not limited to adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. Examples of such functional sequences include polynucleotide, e.g., DNA or RNA, sequences comprising transcriptional and translational initiation and termination regulatory sequences, including promoters (e.g., strong promoters, inducible promoters, and the like) and enhancers which are active in muscle cells.

Also included as part of the functional sequences is an open reading frame (polynucleotide sequence) encoding a protein of interest; flanking sequences may also be included for site-directed integration. In some situations, the 5'-flanking sequence will allow homologous recombination, thus changing the nature of the transcriptional initiation region, so as to provide for inducible or noninducible transcription to increase or decrease the level of transcription, as an example.

In general, the nucleic acid sequence desired to be expressed by the muscle-derived progenitor cell is that of a structural gene, or a functional fragment, segment or portion of the gene, that is heterologous to the muscle-derived progenitor cell and encodes a desired protein or polypeptide product, for example. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, cell differentiation factors, cell signaling factors and programmed cell death factors. Specific examples include, but are not limited to, genes encoding BMP-2 (rhBMP-2), IL-IRa, Factor IX, and connexin 43.

As mentioned above, a marker may be present for selection of cells containing the vector construct. The marker may be an inducible or non-inducible gene and will generally allow for positive selection under induction, or without induction, respectively. Examples of commonly-used marker genes include neomycin, dihydrofolate reductase, glutamine synthetase, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the muscle-derived cells. Such replication systems are represented by replication-defective adenovirus constructed as described, for example, by G. Acsadi et al., 1994, Hum. Mol. Genet 3:579 584, and by Epstein-Barr virus. Examples of replication defective vectors, particularly, retroviral vectors that are replication defective, are BAG, described by Price et al., 1987, Proc. Natl. Acad. Sci. USA, 84:156; and Sanes et al., 1986, EMBO J., 5:3133. It will be understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

If desired, infectious replication-defective viral vectors may be used to genetically engineer the cells prior to in vivo injection of the cells. In this regard, the vectors may be introduced into retroviral producer cells for amphotropic packaging. The natural expansion of muscle-derived progenitor cells into adjacent regions obviates a large number of injections into or at the site(s) of interest.

In another aspect, the present invention provides ex vivo gene delivery to cells and tissues of a recipient mammalian host, including humans, through the use of MDC, e.g., early progenitor muscle cells, that have been virally transduced using an adenoviral vector engineered to contain a heterologous gene encoding a desired gene product. Such an ex vivo approach provides the advantage of efficient viral gene transfer, which is superior to direct gene transfer approaches. The ex vivo procedure involves the use of the muscle-derived progenitor cells from isolated cells of muscle tissue. The muscle biopsy that will serve as the source of muscle-derived progenitor cells can be obtained from an injury site or from another area that may be more easily obtainable from the clinical surgeon.

It will be appreciated that in accordance with the present invention, clonal isolates can be derived from the population of muscle-derived progenitor cells (i.e., PP6 cells or "slowly adhering" cells using the single plate procedure) using various procedures known in the art, for example, limiting dilution plating in tissue culture medium. Clonal isolates comprise genetically identical cells that originate from a single, solitary cell. In addition, clonal isolates can be derived using FACS analysis as described above, followed by limiting dilution to achieve a single cell per well to establish a clonally isolated cell line. An example of a clonal isolate derived from the PP6 cell population is mc13, which is described in Example 1. Preferably, MDC clonal isolates are utilized in the present methods, as well as for genetic engineering for the expression of one or more bioactive molecules, or in gene replacement therapies.

The MDCs are first infected with engineered viral vectors containing at least one heterologous gene encoding a desired gene product, suspended in a physiologically acceptable carrier or excipient, such as saline or phosphate buffered saline, and then administered to an appropriate site in the host. Consistent with the present invention, the MDCs can be administered to body tissues, including skeletal muscle, as described above. The desired gene product is expressed by the injected cells, which thus introduce the gene product into the host. The introduced and expressed gene products can thereby be utilized to treat, repair, or ameliorate the injury, dysfunction, or disease, due to their being expressed over long time periods by the MDCs of the invention, having long-term survival in the host.

In animal model studies of myoblast-mediated gene therapy, implantation of $10^6$ myoblasts per 100 mg muscle was required for partial correction of muscle enzyme defects (see, J. E. Morgan et al., 1988, J. Neural. Sci. 86:137; T. A. Partridge et al., 1989, Nature 337:176). Extrapolating from this data, approximately $10^{12}$ MDCs suspended in a physiologically compatible medium can be implanted into muscle tissue for gene therapy for a 70 kg human. This number of MDC of the invention can be produced from a single 100 mg skeletal muscle biopsy from a human source (see below). For the treatment of a specific injury site, an injection of genetically engineered MDC into a given tissue or site of injury comprises a therapeutically effective amount of cells in solution or suspension, preferably, about $10^5$ to $10^6$ cells per $cm^3$ of tissue to be treated, in a physiologically acceptable medium.

EXAMPLES

Example 1

MDC Enrichment, Isolation and Analysis According to the Pre-Plating Method

MDCs were prepared as described (U.S. Pat. No. 6,866,842 of Chancellor et al.). Muscle explants were obtained from the hind limbs of a number of sources, namely from 3-week-old mdx (dystrophic) mice (C57BL/10ScSn mdx/mdx, Jackson Laboratories), 4-6 week-old normal female SD (Sprague Dawley) rats, or SCID (severe combined immunodeficiency) mice. The muscle tissue from each of the animal sources was dissected to remove any bones and minced into a slurry. The slurry was then digested by 1 hour serial incubations with 0.2% type XI collagenase, dispase (grade II, 240 unit), and 0.1% trypsin at 37° C. The resulting cell suspension was passed through 18, 20, and 22 gauge needles and centrifuged at 3000 rpm for 5 minutes. Subsequently, cells were suspended in growth medium (DMEM supplemented with 10% fetal bovine serum, 10% horse serum, 0.5% chick embryo extract, and 2% penicillin/streptomycin). Cells were then preplated in collagen-coated flasks (U.S. Pat. No. 6,866,842 of Chancellor et al.). After approximately 1 hour, the supernatant was removed from the flask and re-plated into a fresh collagen-coated flask. The cells which adhered rapidly within this 1 hour incubation were mostly fibroblasts (Z. Qu et al., supra; U.S. Pat. No. 6,866,842 of Chancellor et al.). The supernatant was removed and re-plated after 30-40% of the cells had adhered to each flask. After approximately 5-6 serial platings, the culture was enriched with small, round cells, designated as PP6 cells, which were isolated from the starting cell population and used in further studies. The adherent cells isolated in the early platings were pooled together and designated as PP1-4 cells.

The mdx PP1-4, mdx PP6, normal PP6, and fibroblast cell populations were examined by immunohistochemical analysis for the expression of cell markers. The results of this analysis are shown in Table 1.

TABLE 1

Cell markers expressed in PP1-4 and PP6 cell populations.

| | mdx PP1-4 cells | mdx PP6 cells | nor PP6 cells | fibroblasts |
|---|---|---|---|---|
| desmin | +/− | + | + | − |
| CD34 | − | + | + | − |
| Bcl-2 | (−) | + | + | − |
| Flk-1 | na | + | + | − |
| Sca-1 | na | + | + | − |
| M-cadherin | −/+ | −/+ | −/+ | − |
| MyoD | −/+ | +/− | +/− | − |
| myogenin | −/+ | +/− | +/− | − |

Mdx PP1-4, mdx PP6, normal PP6, and fibroblast cells were derived by preplating technique and examined by immunohistochemical analysis.
"−" indicates less than 2% of the cells showed expression;
"(−)"; "−/+" indicates 5-50% of the cells showed expression;
"+/−" indicates ~40-80% of the cells showed expression;
"+" indicates that >95% of the cells showed expression;
"nor" indicates normal cells;
"na" indicates that the immunohistochemical data is not available.

It is noted that both mdx and normal mice showed identical distribution of all the cell markers tested in this assay. Thus, the presence of the mdx mutation does not affect the cell marker expression of the isolated PP6 muscle-cell derived population.

MDCs were grown in proliferation medium containing DMEM (Dulbecco's Modified Eagle Medium) with 10% FBS (fetal bovine serum), 10% HS (horse serum), 0.5% chick embryo extract, and 1% penicillin/streptomycin, or fusion medium containing DMEM supplemented with 2% fetal bovine serum and 1% antibiotic solution. All media supplies were purchased through Gibco Laboratories (Grand Island, N.Y.).

Example 2

MDC Enrichment, Isolation and Analysis According to the Single Plate Method Populations of rapidly- and slowly-adhering MDCs were isolated from skeletal muscle of a mammalian subject. The subject may be a human, rat, dog or other mammal. Biopsy size ranged from 42 to 247 mg.

Skeletal muscle biopsy tissue is immediately placed in cold hypothermic medium (HYPOTHERMOSOL® (BioLife) supplemented with gentamicin sulfate (100 ng/ml, Roche)) and stored at 4° C. After 3 to 7 days, biopsy tissue is removed from storage and production is initiated. Any connective or non-muscle tissue is dissected from the biopsy sample. The remaining muscle tissue that is used for isolation is weighed. The tissue is minced in Hank's Balanced Salt Solution (HBSS), transferred to a conical tube, and centrifuged (2,500×g, 5 minutes). The pellet is then resuspended in a Digestion Enzyme solution (Liberase Blendzyme 4 (0.4-1.0 U/mL, Roche)). 2 mL of Digestion Enzyme solution is used per 100 mg of biopsy tissue and is incubated for 30 minutes at 37° C. on a rotating plate. The sample is then centrifuged (2,500×g, 5 minutes). The pellet is resuspended in culture medium and passed through a 70 µm cell strainer. The culture media used for the procedures described in this Example was Cambrex Endothelial Growth Medium EGM-2 basal medium supplemented with the following components: i. 10% (v/v) fetal bovine serum, and ii. Cambrex EGM-2 SingleQuot Kit, which contains: Insulin Growth Factor-1 (IGF-1), Basic Fibroblast Growth Factor (bFGF), Vascular Endothelial Growth Factor (VEGF), Epidermal Growth Factor (EGF), Hydrocortisone, Heparin, and Ascorbic Acid. The filtered cell solution is then transferred to a T25 culture flask and incubated for 30-120 minutes at 37° C. in 5% $CO_2$. Cells that attach to this flask are the "rapidly-adhering cells".

After incubation, the cell culture supernatant is removed from the T25 flask and placed into a 15 mL conical tube. The T25 culture flask is rinsed with 2 mL of warmed culture medium and transferred to the aforementioned 15 mL conical tube. The 15 mL conical tube is centrifuged (2,500×g, 5 minutes). The pellet is resuspended in culture medium and transferred to a new T25 culture flask. The flask is incubated for ~2 days at 37° C. in 5% CO2 (cells that attach to this flask are the "slowly-adhering cells"). After incubation, the cell culture supernatant is aspirated and new culture medium is added to the flask. The flask is then returned to the incubator for expansion. Standard culture passaging is carried out from here on to maintain the cell confluency in the culture flask at less than 50%. Trypsin-EDTA (0.25%, Invitrogen) is used to detach the adherent cells from the flask during passage. Typical expansion of the "slowly-adhering cells" takes an average of 17 days (starting from the day production is initiated) to achieve an average total viable cell number of 37 million cells.

Once the desired cell number is achieved, the cells are harvested from the flask using Trypsin-EDTA and centrifuged (2,500×g, 5 minutes). The pellet is resuspended in BSS-P solution (HBSS supplemented with human serum albumin (2% v/v, Sera Care Life)) and counted. The cell solution is then centrifuged again (2,500×g, 5 minutes), resuspended with Cryopreservation Medium (CryoStor (Biolife) supplemented with human serum albumin (2% v/v, Sera Care Life Sciences)) to the desired cell concentration, and packaged in the appropriate vial for cryogenic storage. The cryovial is placed into a freezing container and placed in the −80° C. freezer. Cells are administered by thawing the frozen cell suspension at room temperature with an equal volume of physiologic saline and injected directly (without additional manipulation). The lineage characterization of the slowly adhering cell populations shows: Myogenic (87.4% CD56+, 89.2% desmin+), Endothelial (0.0% CD31+), Hematopoietic (0.3% CD45+), and Fibroblast (6.8% CD90+/CD56−).

Following disassociation of the skeletal muscle biopsy tissue, two fractions of cells were collected based on their rapid or slow adhesion to the culture flasks. The cells were then expanded in culture with growth medium and then frozen in cryopreservation medium ($3 \times 10^5$ cells in 15 µl) in a 1.5 ml eppendorf tube. For the control group, 15 µl of cryopreservation medium alone was placed into the tube. These tubes were stored at −80° C. until injection. Immediately prior to injection, a tube was removed from storage, thawed at room temperature, and resuspended with 15 µl of 0.9% sodium chloride solution. The resulting 30 µl solution was then drawn into a 0.5 cc insulin syringe with a 30 gauge needle. The investigator performing the surgery and injection was blinded to the contents of the tubes.

Cell count and viability was measured using a Guava flow cytometer and Viacount assay kit (Guava). CD56 was measured by flow cytometry (Guava) using PE-conjugated anti-CD56 antibody (1:50, BD Pharmingen) and PE-conjugated isotype control monoclonal antibody (1:50, BD Pharmingen). Desmin was measured by flow cytometry (Guava) on paraformaldehyde-fixed cells (BD Pharmingen) using a monoclonal desmin antibody (1:100, Dako) and an isotype control monoclonal antibody (1:200, BD Pharmingen). Fluorescent labeling was performed using a Cy3-conjugated anti-mouse IgG antibody (1:250, Sigma). In between steps, the cells were washed with permeabilization buffer (BD Pharmingen). For creatine kinase (CK) assay, $1 \times 10^5$ cells were plated per well into a 12 well plate in differentiation-inducing medium. Four to 6 days later, the cells were harvested by trypsinization and centrifuged into a pellet. The cell lysis supernatant was assayed for CK activity using the CK Liqui-UV kit (Stanbio).

Example 3

Augmentation of Skeletal Muscle with MDCs

Populations of human muscle derived cells (hMDCs) isolated from human muscle biopsies by way of the preplate technique were tested to show that hMDCs had similar myogenic and regenerative characteristics to their murine counterparts.

Methods.

Pre-Plate Technique: This technique is disclosed throughout the application and specifically, above in Example 1.

Isolation and Cell Culture: Candidate populations were obtained using the pre-plate technique. These cells were grown in EGM™-2 media (Cambrex) at a density of 600 cells/cm² and passaged every 72-96 hours before confluence under standard conditions (5.0% $CO_2$, 37° C.).

Flow Cytometry: hMDC were analyzed for the presence of the cell surface cluster of differentiation markers CD34, CD56, CD144, and CD146.

Immunochemistry: hMDC were stained for desmin, myosin heavy chain, and dystrophin.

Bioinformatic Live Cell Imaging: Cells were grown in a cell culture system with dynamic imaging. Images were taken at 10-min. intervals. We measured numerous parameters such as doubling rate, growth rate, total cell number, elongation, area, and perimeter for the various populations at early passage and late passage. We compared human MDC phenotypic profiles among the different preplate fractions to identify both molecular and behavioral characteristics that might predict in vivo regeneration efficiency.

In vivo regeneration: We transplanted early passage human populations into the gastrocnemius muscles of mdx/SCID mice. We harvested the muscles 2 weeks after transplantation. The muscles were frozen sectioned into 10-µm sections. For immunohistochemical analysis, we used mouse anti-human or anti-mouse dystrophin (Novocastra, DYS3/2, 1:50), biotinylated goat anti-mouse secondary Ab (Vector, 1:500) and streptavidin-Cy3 (Sigma, 1:500). We used a human nuclear antigen antibody to label human nuclei in the skeletal muscle sections.

Results.

We examined 3 preplate fractions—preplates 1 and 2 (pp1-2), preplates 2-3 (pp2-3) and preplates 5-6). All populations were negative for CD34 and CD144, and positive for CD56 and CD146. Over time, a decrease in CD56 and CD146 was observed. Immunostaining revealed the myogenic potential of the cells, as they displayed the ability to fuse into multi-nucleated myotubes, and showed desmin, myosin, and dystrophin expression.

Time-elapsed imaging showed much variability in parameters such as cellular division time, population doubling time, cellular motility behavior, and morphological parameters. We observed media-specific changes in morphology. Cells grown in EGM2 showed a decrease in proliferation rates as cells were expanded. Our analysis to date has no shown any differences in these behaviors which are related to preplate fraction.

Figure 1:
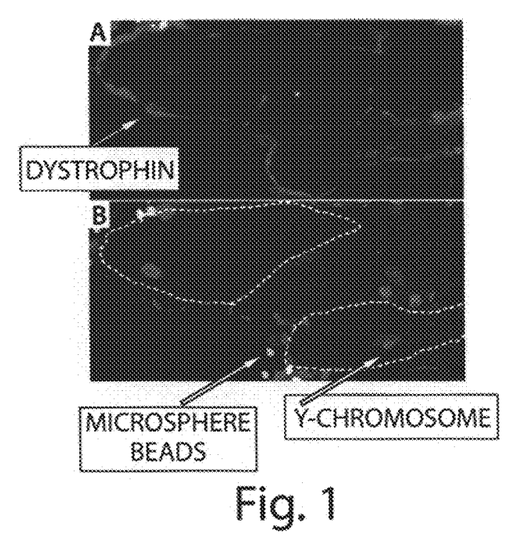
FIGS. 1A and 1B show micrographs of human MDCs (hMDCs) injected into mouse muscle with human dystrophin and mouse Y-chromosome stained to show chimerism in the human and mouse muscle cells that have fused.
Figure 2:
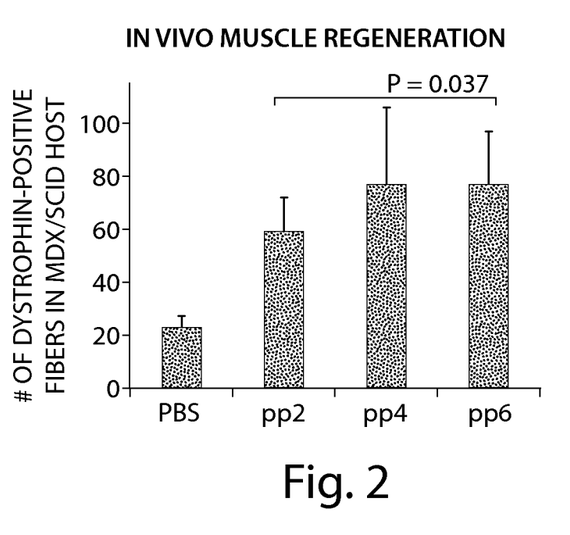
FIG. 2 is a bar graph showing the percentage of dystrophin positive fibers in mice injected with hMDCs.

We injected several preplate populations; pp2 (n=11 muscles), pp4 (n=19), pp6 (n=20). Sex-crossed transplantation of the hMDC to host mdx-scid muscle resulted in fusion of the donor cells to the host skeletal muscle fibers and subsequent delivery and expression of dystrophin in the host. Chimerism was determined by use of the human specific antibody, and donor specific Y-chromosome (FIG. 1). The number of regenerating dystrophin positive fibers was significantly higher in transplantations using pp6 fraction as compared to pp2 fraction (P 0.037, 2-tailed 2-test, FIG. 2). However, there was no significant difference in the level of regeneration between pp2 and pp4 transplantations. All groups had dystrophin levels greater than the PBS sham controls (FIG. 2).

This study shows that hMDCs are similarly obtained from the pp6 which appears to be distinct from pp2 obtained from human muscle biopsy. In the transplantation study, we observe human dystrophin expression, although the number of dystrophin positive regenerating muscle fibers was lower than what has been observed with mouse MDCs. Initial results show that culture in SkGM yields greater proliferation of hMDCs than culture in either EGM-2 or DMEM. Ongoing imaging studies will determine whether this increase in growth is coupled with greater therapeutic efficacy and differing cellular phenotypes.

We claim:

1. A method of augmenting a skeletal muscle in a mammal suffering from a muscle pathology comprising:
   a) isolating muscle-derived progenitor cells (MDCs) by a method comprising:
      (i) isolating skeletal muscle from a human;
      (ii) storing the skeletal muscle at 4° C. for 5 to 7 days;
      (iii) suspending the human skeletal muscle in a medium in a first cell culture container between 30 and 120 minutes thereby producing a cell population of adherent cells and a population of non-adherent cells;
      (iv) isolating the medium containing a population of non-adherent cells;
      (v) transferring the medium containing the population of the non-adherent cells to a second cell culture container;
      (vi) allowing the population of the transferred non-adherent cells from step (v) to attach to the walls of the second cell culture container, wherein the incubation is for 1 to 3 days;
      (vii) removing the medium from the second container and replacing with new medium after the 1 to 3 days of incubation; and
      (viii) isolating the cells from the walls of the second cell culture container, wherein the isolated cells are MDCs and are desmin+;
   b) expanding the isolated MDCs in culture for between 10 and 20 days; and
   c) administering a therapeutically effective amount of the expanded MDCs to the skeletal muscle in the mammal suffering from a muscle pathology; allowing the MDCS to engraft to the skeletal muscle and thereby augmenting the skeletal muscle in the mammal.

2. The method of claim 1, wherein the mammal is a human.

3. The method of claim 1, wherein the expanded MDCs are administered by injecting the MDCs into the skeletal muscle of the mammal.

4. The method of claim 1, wherein the skeletal muscle of the mammal has a defect.

5. The method of claim 4, wherein the expanded MDCs are administered by applying them onto, into or around the site of the defect.

6. The method of claim 5, wherein the expanded MDCs are applied through injection.

7. A method of augmenting a skeletal muscle in a mammal suffering from a muscle pathology comprising:
   a) isolating muscle-derived progenitor cells (MDCs) by a method comprising:
      (i) isolating skeletal muscle from a human;
      (ii) storing the skeletal muscle at 4° C. for 5 to 7 days;
      (iii) suspending the human skeletal muscle in a medium in a first cell culture container between 30 and 120 minutes thereby producing a cell population of adherent cells and a population of non-adherent cells;
      (iv) isolating the medium containing a population of non-adherent cells;
      (v) transferring the medium containing the population of the non-adherent cells to a second cell culture container;
      (vi) allowing the population of the transferred non-adherent cells from step (v) to attach to the walls of the second cell culture container, wherein the incubation is for 1 to 3 days;
      (vii) removing the medium from the second container and replacing with new medium after the 1 to 3 days of incubation; and
      (viii) isolating the cells from the walls of the second cell culture container, wherein the isolated cells are MDCs and are desmin+;
   b) expanding the isolated MDCs in culture for between 10 and 20 days;
   c) freezing the isolated MDCs to a temperature between about −25° C. and −90° C.;
   d) thawing the frozen isolated MDCs at room temperature with an equal volume of physiologic saline;
   and e) administering the thawed MDCs to the skeletal muscle in the mammal suffering from a muscle pathology; allowing the MDCS to engraft to the skeletal muscle and thereby augmenting the skeletal muscle in the mammal.

8. The method of claim 7, wherein the mammal is a human.

9. The method of claim 7, wherein the expanded MDCs are administered by injecting the MDCs into the skeletal muscle of the mammal.

10. The method of claim 7, wherein the skeletal muscle of the mammal has a defect.

11. The method of claim 10, wherein the expanded MDCs are administered by applying them onto, into or around the site of the defect.

12. The method of claim 11, wherein the MDCs are applied through injection.

* * * * *